United States Patent
Fledelius et al.

(10) Patent No.: US 6,300,083 B1
(45) Date of Patent: *Oct. 9, 2001

(54) ASSAYING D-AMINO ACIDS IN BODY FLUIDS

(75) Inventors: Christian Fledelius; Paul Cloos, both of Copenhagen; Per Qvist, Klampenborg, all of (DK)

(73) Assignee: Osteometer Biotech A/S, Herlev (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/242,721

(22) PCT Filed: Aug. 12, 1997

(86) PCT No.: PCT/EP97/04372

§ 371 Date: Jan. 10, 2000

§ 102(e) Date: Jan. 10, 2000

(87) PCT Pub. No.: WO98/08098

PCT Pub. Date: Feb. 26, 1998

(30) Foreign Application Priority Data

Aug. 22, 1996 (GB) .................................................. 9617616

(51) Int. Cl.[7] .................................................. G01N 33/53
(52) U.S. Cl. ........................ 435/7.1; 435/7.92; 435/7.94; 435/7.95; 435/7.93; 435/331; 436/518; 436/532; 530/323; 530/326; 530/327; 530/328; 530/329; 530/356; 530/388.1; 530/389.1
(58) Field of Search ................................... 435/7.1, 7.92, 435/7.94, 7.95, 7.93, 331; 436/518, 532; 530/323, 326, 327, 328, 329, 356, 388.1, 389.1

(56) References Cited

U.S. PATENT DOCUMENTS

| | | |
|---|---|---|
| 3,600,132 | 8/1971 | Goverde . |
| 4,312,853 | 1/1982 | Timpl . |
| 4,504,587 | 3/1985 | Timpl et al. . |
| 4,628,027 | 12/1986 | Gay . |
| 4,778,768 | 10/1988 | Heinegård et al. . |
| 4,973,666 | 11/1990 | Eyre . |
| 5,001,225 | 3/1991 | Taylor . |
| 5,140,103 | 8/1992 | Eyre . |
| 5,300,434 | 4/1994 | Eyre . |
| 5,320,970 | 6/1994 | Eyre . |
| 5,455,179 | 10/1995 | Eyre . |
| 5,472,884 | 12/1995 | Eyre . |
| 5,473,052 | 12/1995 | Eyre . |
| 5,532,169 | 7/1996 | Eyre . |
| 5,576,189 | 11/1996 | Eyre . |
| 5,607,862 | 3/1997 | Eyre . |
| 5,641,837 | 6/1997 | Eyre . |
| 5,652,112 | 7/1997 | Eyre . |
| 5,656,439 | 8/1997 | Eyre . |
| 5,679,583 | 10/1997 | Brocks et al. . |
| 5,763,272 | 6/1998 | Naser et al. . |
| 5,821,065 | 10/1998 | Naser et al. . |
| 5,834,221 | 11/1998 | Eyre . |
| 5,912,131 | 6/1999 | Eyre . |
| 5,939,274 | 8/1999 | Eyre . |
| 5,962,639 | 10/1999 | Eyre . |
| 6,107,047 | * 8/2000 | Fledelius et al. ...................... 435/7.1 |
| 6,117,646 | * 9/2000 | Qvist et al. .......................... 435/7.93 |

FOREIGN PATENT DOCUMENTS

| | | |
|---|---|---|
| 42 25 038 | 2/1994 | (DE) . |
| 0 298 210 | 1/1989 | (EP) . |
| 0 339 443 | 11/1989 | (EP) . |
| 0 303 715 | 2/1990 | (EP) . |
| 0 424 428 | 5/1991 | (EP) . |
| 0 465 104 | 1/1992 | (EP) . |
| 0 502 928 | 9/1992 | (EP) . |
| 0 505 210 | 9/1992 | (EP) . |
| 0 394 296 | 1/1995 | (EP) . |
| 0 704 458 | 4/1996 | (EP) . |
| 0 718 309 | 6/1996 | (EP) . |
| 0 829 724 | 3/1998 | (EP) . |
| 2 205 643 | 12/1988 | (GB) . |
| WO 83/04104 | 11/1983 | (WO) . |
| WO 88/08980 | 11/1988 | (WO) . |
| WO 89/04491 | 5/1989 | (WO) . |
| WO 89/12824 | 12/1989 | (WO) . |
| WO 90/04417 | 5/1990 | (WO) . |
| WO 90/08195 | 7/1990 | (WO) . |
| WO 91/08478 | 6/1991 | (WO) . |
| WO 91/09114 | 6/1991 | (WO) . |
| WO 92/21698 | 12/1992 | (WO) . |
| WO 94/03813 | 2/1994 | (WO) . |
| WO 94/14844 | 7/1994 | (WO) . |
| WO 95/04282 | 2/1995 | (WO) . |
| WO 95/08115 | 3/1995 | (WO) . |
| WO 96/12193 | 4/1996 | (WO) . |
| WO 96/30765 | 10/1996 | (WO) . |
| WO 96/36645 | 11/1996 | (WO) . |
| WO 98/08098 | 2/1998 | (WO) . |

OTHER PUBLICATIONS

International Search Report date Jun. 16, 1998 of Int'l Appl. No. PCT/EP97/06803.

Ala–Kokko et al., 1989, "Structure of cDNA Clones Coding for the Entire Preproα1(III) Chain of Human Type III Procollagen", *Biochem. J.* 260:509–516.

Ala–Kokko et al., 1990, "Single Base Mutation in the Type II Procollagen Gene (COL2A1) as a Cause of Primary Osteoarthritis Associated with a Mild Chondrodysplasia", *Proc. Natl. Acad. Sci.* 87:6565–6586.

Astaldi et al., 1980, "Human Endothelial Culture Supernatant (HECS): A Growth Factor for Hybridomas", *J. Immunol.* 125(4): 1411–1414.

(List continued on next page.)

*Primary Examiner*—Jeffrey Stucker
(74) *Attorney, Agent, or Firm*—Pennie & Edmonds LLP

(57) ABSTRACT

The rate of degradation in vivo of a body protein is determined by measuring the amount of a D-amino acid containing fragment of the protein in a body fluid using an antibody capable of discriminating between the D-amino acid containing fragment and its L-amino acid containing analogue.

18 Claims, 2 Drawing Sheets

OTHER PUBLICATIONS

Baldwin et al., 1989, "Structure of cDNA Clones Coding for Human Type II Procollagen", *Biochem. J.* 262:521–528.

Beardsworth et al., 1990, "Changes with Age in the Urinary Excretion of Lysyl– and Hydroxylysylpyridinoline, Two New Markers of Bone Collagen Turnover", *J. Bone Miner. Res.* 5:671–676.

Bernard et al., 1983, "Nucleotide Sequences of Complementary Deoxyribonucleic Acids for the Pro$\alpha$1 Chain of Human Type I Procollagen. Statistical Evaluation of Structures That Are Conserved during Evolution", *Biochemistry* 22:5213–5223.

Black et al., 1988, "Quantitative Analysis of the Pyridinium Crosslinks of Collagen in Urine Using Ion–Paired Reversed-Phase High–Performance Liquid Chromatography", *Ana. Biochem.* 169:197–203.

Black et al., 1989, "Urinary Excretion of the Hydroxypyridinium Cross Links of Collagen in Patients with Rheumatoid Arthritis", *Annals of the Rheumatic Diseases* 48:641–644.

Bonde et al., 1994, "Crosslaps™ ELISA Plus—An Immunoassay for the Measurement of Degradation Products of Type I Collagen in Serum" *J. Bone and Min. Res.* 9(1) Abst. B178, p. S274.

Bonde et al., 1994, "An Immunoassay (Crosslaps™ ELISA) for Quantification of Type I Collagen Degradation Products in Urine" *J. Bone and Min. Res.* 9(1) Abst. C368, p. S406.

Bonde et al., 1994, "Immunoassay for Quantifying Type 1 Collagen Degradation Products in Urine Evaluated", *Clin. Chem.* 40(11):2022–2025.

Bonde et al., 1995, "Measurement of Bone Degradation Products in Serum Using Antibodies Reactive with an 8 Amino Acid Sequence of the C–Telopeptides of Type I Collagen", *J. of Bone and Min. Res.* 10(1) Abstract S481, p. 5271.

Bonde et al., 1995, "A Coated Tube Radio Immunoassay (RIA) for the Measurement of Bone Degradation Products in Urine Using a Monoclonal Antibody Reactive with an 8 Amino Acid Sequence of the C–Telopeptides of Type I Collagen" *J. Bone and Min. Res.* 10(1) Abst. S475, p. S269.

Bonde et al., 1995, "Effect of Bisphosphonate Therapies (Pamidronate and Ibandronate) on the Excretion of Degradation Product of the C–Telopeptides of Type I Collagen Measured by a Radioimmunoassay (Crosslaps™ RIA)" *Bone* 17(6) Abst. 45, p. 609.

Bonde et al., 1995, "Applications of an Enzyme Immunoassay for a New Marker of Bone Resorption . . . ", *J. Clinical Endocrinology and Metabolism,* 80(3):864–868. (Crosslaps): Follow–up on Hormone Replacement Therapy, and Osteoporosis Risk Assessment, 867 & 868.

Brennan et al., 1993, "Spontaneous Degradation of Polypeptides at Aspartyl and Asparaginyl Residues: Effects of the Solvent Dielectric", *Protein Science* 2:331–338.

Capecchi et al., 1983, "Critical Examination of a Method for the Analysis of $\alpha$ and $\omega$ Linkages in Peptides Containing Aspartic Acid and Glutamic Acid", *J. Org. Chem.* 48:2014–2021.

Christgau et al., 1995, "Effect of Bisphosphonate Treatment on the Serum Concentration of Two Collagen Derived Biochemical Markers of Bone Metabolism" *Bone* 17(6) Abst. 48, p. 609.

Christiansen et al., "Prediction of Future Fracture Risk", Center for Clinical and Basic Research,Osteopress Aps 1993; pp. 52–54.

Chu et al., 1984, "Human Pro$\alpha$1(I) Collagen Gene Structure Reveals Evolutionary Conservation of a Pattern of Itrons and Exons", *Nature* 310:337–340.

Click et al., 1970, "Isolation and Characterization of the Cyanogen Bromide Peptides from the $\alpha$1 and $\alpha$2 Chains of Human Skin Collagen", *Biochemistry* 9:4699–4706.

de Wet et al., 1987, "Organization of the Human Pro–$\alpha$2(I) Collagen Gene", *J. Biol. Chem.* 262:16032–16036.

del Pozo et al., 1986, "Binding of 1–anilinoaphthalene–8–sulfonic acid to type I collagen" *Int. J. Pept. Protein Res.* 28:173–178.

Delmas, P. et al., 1986, "Serum Bone GLA–Protein in Growth Hormone Deficient Children", *J. Bone Min. Res.* 1:333–338.

Delmas, P.D., 1990, "Biochemical Markers of Bone Turnover for the Clinical Assessment of Metabolic Bone Disease", *Metabolic Bone Dis.* 19:1–18.

Dickson et al., 1993, "Pyridinolines and Cross–linked Type I Collagen N–telopeptides as Markers of Bone Metastases in Breast Cancer", 15th Annual Mtg of the Amer. Soc. for Bone & Min. Res., Tampa, Fl., Sep., 8:S288, Abstr. 686.

Dodge et al., 1989, "Immunohistochemical Detection and Immunochemical Analysis of Type II Collagen Degradation in Human Normal, Rheumatoid, and Osteoarthritic Articular Cartilages and in Explants of Bovine Articular Cartilage Cultured with Interleukin 1", *J. Clin. Invest.* 83:647–661.

Eyre et al., 1984, "Quantitation of Hydroxypyridinium Crosslinks in Collagen by High–Performance Liquid Chromatography", *Analytical Biochemistry* 137:380–388.

Eyre et al., 1988, "Identification of Urinary Peptides Derived from Cross–linking Sites in Bone Collagen in Paget's Disease", *J. of Bone & Mineral Res* 3:S210, Abstr. 565.

Eyre, D.R., 1984, "Cross–linking in Collagen and Elastin", *Ann. Rev. Biochem.* 53:717–748.

Eyre, D.R., 1994, "New Molecular Markers of Bone Metabolism", *Therapeutic Research* (Symposium) 15(2):532–535.

Fledelius et al., 1994, "Estimation of Bone Resorption Using Monoclonal Antibodies to Human Type I Collagen", *Am. Soc. of Bone and Min. Res.,* Abst. C344.

Fledelius et al., 1995, "Effects of Anti–Resorptive Therapies on Two Immunoassays Specific for an B Amino Acid Sequence Found in Urinary Degradation Products from the C–Telopeptides of Type I Collagen" *J. Bone and Min. Res.* 10(1) Abst. S482, p. S271.

Fledelius et al., 1995, "Effect of Bisphosphonate Treatment on the Urinary Excretion of C–Telopeptide Degradation Products of Type I Collagen Measured in the Crosslaps™ ELISA" *Bone* 17(6) Abst. 53, p. 611.

Foged et al, 1994, "Bone Resorption In Vitro Characterized by ELISA" *J. Bone and Min. Res.* 9(1) Abst. B60, p. S245.

Fujimoto, D., 1980, "Evidence for Natural Existence of Pyridinoline Crosslink in Collagen", *Biochem. & Biophys. Res. Comm.* 93:948–953.

Fujimoto et al., 1983, "Analysis of Pyridinoline, a Cross–Linking Compound of Collagen Fibers, in Human Urine", *J. Biochem.* 94:1133–1136.

Furthmayr, H., 1982, "Immunization Procedures, Isolation by Affinity Chromatography, and Serological and Immunochemical Characterization of Collagen Specific Anitbodies", *Immunochemistry of the Extracellular Matrix,* H. Furthmayr (ed.) CRC Press, vol. 1, Chap. 11, pp. 143–178.

Galletti, P. et al., 1995, "Protein Damage and Methylation-Mediated Repair in the Erythrocyte" *Biochem. J.* 306:313–325.

Garnero et al., 1994, "Assessment of Bone Resportion with a New Marker of Collagen Degradation in Patients with Metabolic Bone Disease", *J. Clin. Endo. and Met.* 79(3):780–785.

Garnero et al., 1994, "Different Effects of Bisphosphonate and Estrogen Therapy on the Excretion of Free and Peptide–Bound Crosslinks", *Amer. Soc. of Bone and Min. Res.,* Abst. 134.

Garnero et al., 1996, "Markers of Bone Resorption Predict Hip Fracture in Elderly Women: The EPIDOS Prospective Study", *J. of Bone Miner. Res.* 11(10):1531–1538.

Geiger et al., 1987, "Deamidation, Isomerization, and Racemization at Asparaginyl and Aspartyl Residues in Peptides" *J. Biol. Chem.,* 262(2):785–794.

Gertz et al., 1994, "Monitoring Bone Resorption in Early Postmenopausal Women by an Immunoassay for Cross–Linked Collagen Peptides in Urine", *J. of Bone & Min. Res.* 9(2):135–142.

Gundersen, V. et al., 1993, Demonstration of Glutamate/Aspartate Uptake Activity in Nerve Endings by Use of Antibodies Recognizing Exogenous D–Aspartate, *Neuroscience,* 57(1):97–111.

Gunja–Smith et al, 1981 "Collagen Cross–linking Compounds in Human Urine", *Biochem. J.* 197:759–762.

Hanson et al., 1992, "A Specific Immunoassay for Monitoring Human Bone Resorption: Quantitation of Type I Collagen Cross–linked N–Telopeptides in Urine",*J. of Bone & Min. Res.* 7:1251–1258.

Hassager et al., 1994, "The Carboxy–Terminal Pyridinoline Cross–linked Telopeptide of Type I Collagen in Serum as a Marker of Bone Resorption: The Effect of Nandrolone Decanoate and Hormone Replacement Therapy", *Calcif. Tissue Int.* 54:30–33.

Henkel et al., 1987, "Characterisation of a Type–I Collagen Trimeric Cross–linked Peptide from Calf Aorta and its Cross–Linked Structure", *Eur. J. Biochem.* 165:427–436.

Ishikawa, E. et al., 1983, "Enzyme–Labeling of Antibodies and Their Fragments for Enzyme Immunoassay and Immunohistochemical Staining", *Journal of Immunoassay* 4(3):209–327.

Janeczko et al., 1989, "Nucleotide and Amino Acid Sequences of the Entire Human α1 (III) Collagen", *Nucl. Acids Res.* 17:6742.

Kearney et al., 1979, "A New Mouse Myeloma Cell Line That has Lost Immunoglobulin Expression but Permits the Construction of Antibody–secreting Hybrid Cell Lines", *J. Immunol.* 123(4): 1548–1550.

Kivirikko, K.I., 1970, "Urinary Excretion of Hydroxyproline in Health and Disease", *Int. Rev. Connect. Tissue Res.* 5:93–163.

Krane et al., 1981, "Organic Matrix Defects in Metabolic and Related Bone Diseases", *Develop. Biochem.* 22:185–194.

Krüger–Franke, 1991, "Pyridinoline–containing collagen degradation products in the urine of patients with osteoarthrosis of the hip joint", *Z. Rheumatol.* 50:323–327 (German with English Translation).

Kuboki et al., 1981, "Location of the Intermolecular Cross–links in Bovine Dentin Collagen, Solubilization with Trypsin and Isolation of Cross–link Peptides Containing Dihydroxylysinonorleucine and Pyridinoline", *Biochem. & Biophys. Res. Comm.* 102:119–126.

Kuhn, K., 1982, "Chemical Properties of Collagen", *Immunochemistry of the Extracellular Matrix,* H. Furthmayr (ed.), CRC Press, 1(1)1–29.

Kühn, K., 1987, "The Classical Collagens: Types I, II, and III", *Structure & Function of Collagen Types,* Mayne & Bergeson (eds.), Academic Press, pp. 1–42.

Kuypers et al., 1992, "Identification of the Loci of the Collagen–associated Ehrlich Chromogen in Type I Collagen Confirms Its Role as a Trivalent Cross–link", *Biochem. J.* 283:129–136.

Last et al., 1990, "Biosynthesis of Collagen Crosslinks", *Int. J. Biochem.,* 22(6):559–564.

Lehrman et al., 1992, "Identification and Characterization of an Anti–Isoaspartic Acid Monoclonal Antibody", *Journ. Of Prot. Chem.* 11(6):657–663.

Loidl et al., 1984, "Molecular Cloning and Carboxyl-–propeptide Analysis of Human Type III Procollagen", *Nucl. Acids. Res.,* 12(24):9383–9394.

Lowenson et al., 1988, Does the Chemical Instability of Aspartyl and Asparaginyl Residues in Proteins Contribe to Erythrocyte Aging?, *Blood Cells* 14:103–117.

Macek et al., 1987, "Determination of Collagen Degradation Products in Human Urine in Osteoarthrosis", *Z. Rheumatol.* 46:237–240.

McClung et al., 1996, "Inability of Baseline Biochemical Markers to Predict Bone Density Changes in Early Postmenopausal Women", *J. of Bone Miner. Res.* 11(S1):S127.

Morein et al., 1984, "Iscom, a Novel Structure for Antigenic Presentation of Membrane Proteins from Enveloped Viruses", *Nature* 308:457–460.

Morgan et al., 1970, "A Comparative Study of Glycopeptides Derived from Selected Vertebrate Collagens", *J. Biol. Chem.* 245:5042–5048.

Nakane et al., 1974, "Peroxidase–labeled Antibody: a New Method of Conjugation", *J. Histochem. Cytochem.* 22(12):1084–1091.

Niemelä, O., 1985, "Radioimmunoassays for Type III Procollagen Amino–Terminal Peptides in Humans", *Clin. Chem.* 31(8):1301–1304.

Oliyai et al., 1994, "Chemical Pathways of Peptides Degradation. VI. Effect of the Primary Sequence on the Pathways of Degradation of Aspartyl Residues in Model Hexapeptides", *Pharm. Res.* 11(5):751–758.

Otter et al., 1988, "Type I Collagen α–1 Chain C–Telopeptide: Solution Structure Determined by 600–MHz Proton NMR Spectroscopy and Implications for Its Role in Collagen Fibrillogenesis", *Biochem.* 27:3560–3567.

Otter et al., 1989, A $^1$H and $^{13}$C NMR Study on the Role of Salt–Bridges in the Formation of a Type I β–Turn in N–Actyl–L–Asp–L–Glu–L–Lys–L–Ser–NH$_2$, *J. Biomol. Struct. Dyn.* 7(3):455–476.

Overgard et al., 1994, "A New Biochemical Marker for Determination of the Optimum Treatment Regimen of Nasal Calcitonin and the Effect on Fracture Rates", *J. Bone and Min. Res.* 9(1) Abst. C342, p. S403.

Pierard et al., 1984, "Radioimmunoassay for the Amino-–Terminal Sequences of Type III Procollagen in Human Body Fluids Measuring Fragmented Precursor Sequences", *Anal. Biochem.* 141:127–136.

Qvist et al., 1994, "Use of a New Biochemical Marker (Crosslaps™) for the Estimation of Rate of Postmenopausal Bone Loss", *Am. Soc. Bone and Min. Res*, Abst. B419.

Ravn et al., 1994, "High Bone Turnover is Associated with Low Bone Mass in Both Pre–and Postmenopausal Women" *J. Bone and Min. Res.* 9(1) Abst. A216, p. S190.

Ravn et al., 1995, "The Effect on Bone Mass and Bone Markers of Different Doses of Ibandronate—A New Bisphosphonate for Prevention and Treatment of Postmenopausal Osteoporosis, A 1-Year Randomized, Double–Blind, Placebo–Controlled Dose–Finding Study" *Bone* 17(6) Abst. 74, p. 616.

Rennard et al., 1980, "Enzyme–Linked Immunoassay (ELISA) for Connective Tissue Components", *Anal. Biochem.* 104:205–214.

Riggs et al., 1992, "The Prevention and Treatment of Osteoporosis", *New England J. of Med.* 327(9):620–627.

Risteli et al., 1986, "Radioimmunoassay for Monitoring Connective Tissue Metabolism", *Rheumatol.* 10:216–245.

Risteli et al., 1993, "Radioimmunoassay for the Pyridinoline Cross–Linked Carboxy–Terminal Telopeptide of Type I Collagen: A New Serum Marker of Bone Collagen Degradation", *Clin. Chem.* 39:635–640.

Risteli et al., 1997, "Assays of Type I Procollagen Domains and Collagen Fragments: Problems to be Solved and Future Trends", *Scand J Clin Lab Invest* 57(Suppl 227):105–113.

Robins, S.P., 1982, "An Enzyme–linked Immunoassay for the Collagen Cross–link Pyridinoline", *Biochem. J.* 207:617–620.

Robins et al., 1986, "Measurement of the Cross Linking Compounds, Pyridinoline, in Urine as an Index of Collagen Degradation in Joint Disease", *Annals of the Rheum. Diseases* 45:969–973.

Robins et al., 1987, "Measurement of Hydroxypyridinium Crosslinks of Collagen as an Index of Bone Matrix Degradation", Paper, Lake Garda, Italy, p. 23, Abstr. OP45.

Rodriguiz et al., 1993, "Type I Collagen Cross–linked N–telopeptide Excretion by Osteopetrotic Patients During Interferon Gamma Therapy: A Correlation with Bone Biochemical and Densitometric Markers", 15th Annual Mtg of the Amer. Soc. for Bone & Min. Res., Tampa, Fl., Sep., 8:S291, Abstr. 698.

Rohde et al., 1979, "Radioimmunoassay for Type III Procollagen Peptide and its Application to Human Liver Disease", *Euro. Jour. of Clin. Invest.* 9:451–459.

Rohde et al., 1983, "Serum and Urine Analysis of the Aminoterminal Procollagen Peptide Type III by Radioimmunoassay with Antibody Fab Fragments", *Collagen Rel. Res.* 3:371–379.

Russell et al., 1981, "Biochemical Markers of Bone Turnover in Pagent's Disease", *Metab. Bone Dis. and Rel. Res.* 4 and 5, 255–262.

Sakai et al., 1997, "D–Aspartic Acid Localization During Postnatal Development of Rat Adrenal Gland", *Biochemical and Biophysical Research Communications*, 235(2):433–436.

Sangiorgi et al., 1985, "Isolation and Partial Characterization of the Entire Human Proα1(II) Collagen Gene", *Nucl. Acids Res.* 13(7):2207–2225.

Schröter–Kermani et al., 1990, "An Inhibition Elisa for the Quantification of Collagens Type I and Type II in Cyanogen Bromide–Digested TissueS Using Fragment–Directed Antibodies", *Immunol. Invest.* 19(5–6):475–491.

Schuppan et al., 1986, "Radioimmunoassay for the Carboxy–terminal Cross–linking domain of Type IV (Basement Membrane) Procollagen in Body Fluids", *J. Clin. Invest.* 78:241–248.

Scott, P.G., 1986, "Spectropic Study of Environment–Dependent Changes in the Conformation of the Isolated Carboxy–Terminal Telopeptide of Type I Collagen", *Biochem.* 25:974–980.

Seibel et al., 1989, "Urinary Hydroxy–pyridinium Crosslinks Provide Indices of Cartilage and Bone Involvement in Arthritic Diseases", *Journ. of Rheumatology* 16(7):964–970.

Singer et al., 1978, "Paget's Disease of Bone", *Metabolic Bone Disease* 2:489–575, (eds. Avioli, L.V. and Kane, S.M., Academic Press, New York.

Soinila et al., 1992, "Immunohistochemistry of Enkephalins: Model Studies on Hapten–Carrier Conjugates and Fixation Methods", *J. Hitochem. Cytochem.* (40)2:231–239.

Su et al., 1989, "Nucleotide Sequence of the Full Length cDNA Encoding for Human Type II Procollagen", *Nucl. Acids. Res.* 17:9473.

Tanaka, 1992, "Urinary Excretion of β–aspertylpeptide in Relation to Collagen Catabolism", Department of Agricultural Chemistry, Utsunomiya University, pp. 26–29 (Japanese and English translation).

Morita, T., 1995, "Urinary excretion of β–aspartylpeptide in relation to collagen catabolism", *Chem. Abstr.* 122:13797, abstr. 122:131800w.

Tellerova et al., 1986, "Determination of Larger Urinary Peptides in Osteoarthrosis by High–Performance Liquid Chromatography", *Scand. J. Rheumatol.* 15:52–56.

Uebelhart et al., 1990, "Urinary Excretion of Pyridinium Crosslinks: A New Marker of Bone Resorption in Metabolic Bone Disease", *Bone and Mineral* 8:87–96.

Vikkula et al., 1989, "Structural Analyses of the Polymorphic Area in Type II Collagen Gene", *FEBS Lett.* 250:171–174.

Weiss et al., 1969, "The Quantitative Relationship of Urinary Peptide Hydroxyproline Excretion to Collagen Degradation", *J. Clin. Invest.* 48:1–10.

Werkmeister et al., 1990, "Characterisation of a Monoclonal Antibody Against Native Human Type I Collagen", *Euro. J. Biochem.*, 187:439–443.

Wu et al., 1984, "Identification of Hydroxypyridinium Cross–Linking Sites in Type II Collagen Bovine Articular Cartilage", *Biochemistry* 23:1850–1857.

* cited by examiner

US 6,300,083 B1

ASSAYING D-AMINO ACIDS IN BODY FLUIDS

FIELD OF THE INVENTION

The present invention relates to the assaying of collagen or other protein degradation products and materials useful therefor.

BACKGROUND OF THE INVENTION

Collagens and Disorders of Collagen Metabolism

Osteoporosis is the most common bone disease in humans. Primary osteoporosis, accompanied by increased susceptibility to fractures, results from a progressive reduction in skeletal bone mass. It is estimated to affect 15–20 million individuals in the USA alone. Its basis is an age-dependant imbalance in bone remodelling, i.e. in the rates of formation and resorption of bone tissue.

In the USA about 1.2 million osteoporosis-related fractures occur in the elderly each year including about 538,000 compression fractures of the spine, about 227,000 hip fractures and a substantial number of early fractured peripheral bones. Between 12 and 20% of the hip fractures are fatal because they cause severe trauma and bleeding, and half of the surviving patients require nursing home care. Total costs from osteoporosis-related injuries now amount to at least $10 billion annually in the USA (Riggs, New England Journal of Medicine, 327:620–627 (1992)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, the availability of reliable assays for measuring bone resorption rates in patients or in healthy subjects is very limited. Other disorders entailing (and correlated with) abnormalities in collagen metabolism include Paget's disease, Marfan's syndrome, osteogenesis imperfecta, neoplastic growth in collagenous tissue, dwarfism, rheumatoid arthritis, osteo-arthritis and vasculitis syndrome.

Three known classes of human collagen have been described to date. The Class I collagens, subdivided into types I, II, III, V, and XI, are known to form fibrils. The amino-acid sequences of types I to III (to the extent they have been elucidated) are given in Appendix A of WO95/08115.

Collagen type I accounts for more than 90% of the organic matrix of bone. Therefore, in principle, it is possible to estimate the rate of bone resorption by monitoring the degradation of collagen type I. Likewise, a number of other disease states involving connective tissue can be monitored by determining the degradation of collagen. Examples are collagen type II degradation associated with rheumatoid arthritis and osteoarthritis and collagen type III degradation in vasculitis syndrome.

Amino acid sequences of human type III collagen, human pro α1(II) collagen, and the entire prepro α1(III) chain of human type III collagen and corresponding cDNA clones have been investigated and determined by several groups of researchers; see Loil et al., Nucleic Acid Research 12:9383–9394 (1984): Sangiorgi et al., Nucleic Acids Research, 13:2207–2225 (1985); Baldwin et al., Biochem J., 262:521–528 (1989); and Ala-Kokko et al., Biochem. J., 260:509–516 (1989).

Type I, II, and III collagens are all formed in the organism as procollagen molecules, comprising N-terminal and C-terminal propeptide sequences, which are attached to the core collagen molecules. After removal of the propeptides, which occurs naturally in vivo during collagen synthesis, the remaining core of the collagen molecules consists largely of a triple-helical domain having terminal telopeptide sequences which are non-triple-helical. These telopeptide sequences have an important function as sites of intermolecular cross-linking of collagen fibrils extra-cellularly. The alpha-helical region also includes crosslinkable sites.

Intermolecular cross-links provide collagen fibrils with biomechanical stability. The formation of these cross-links is initiated by modification of lysine and hydroxylysine residues to the corresponding aldehydes. Several of these residues located on adjacent chains of collagen will spontaneously form different intermolecular cross-links. The exact position of the sites for cross-linking on collagen telopeptides and from the helical region has been previously described. See, for example, Kühn, K., in Immunochemistry of the extracellular matrix, 1:1–29, CRC Press, Inc., Boca Raton, Fla. (1982), Eyre, D. R., Ann. Rev. Biochem., 53:717–48 (1984) or U.S. Pat. Nos. 5,140,103 and 5,455,179. Furthermore, the amino acid sequences of some potential sites for cross-linking in type I, II, and III collagen are given in Table 1 below.

The fibrous proteins, collagen and elastin, are cross-linked by a unique mechanism based on aldehyde formation from lysine or hydroxylysine side chains. Four homologous loci of cross-linking are evident in molecules of type I, II and III collagens (for review see Kühn, K., in Immunochemistry of the extracellular matrix, 1:1–29 (1982)). Two are aldehyde sites, one in each telopeptide region. The other two sites are hydroxylysine symmetrically placed at about 90 residues from each end of the molecule. When collagen molecules pack into fibrils, these latter sites in the helical region align and react with telopeptide aldehydes in adjacent molecules. There is now strong evidence that 3-hydroxypyridinium residues are the mature cross-link coming from hydroxylysine-derived aldehydes. The mature cross-linking residues of the other pathway, i.e. from aldehyde formation of lysine residues, are however, still unknown.

As illustrated by formula in EP-0394296 discussed below, the two 3-hydroxypyridinium cross-links have been found to be hydroxylysyl pyridinoline (also known simply as "pyridinoline") and lysyl pyridinoline (also known as "deoxypyridinoline"). These cross-linking compounds are naturally fluorescent. Some hydroxylysyl pyridinoline cross-link are found to by glycosylated as discussed for instance in EP-A-0424428.

However, as described in Last et al, Int. J. Biochem. Vol. 22, No. 6, pp 559–564, 1990 other crosslinks occur naturally in collagen.

Prior Art Assays for Collagen Degradation

In the past, assays have been developed for monitoring degradation of collagen in vivo by measuring various biochemical markers, some of which have been degradation products of collagen.

For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as discussed further below.

For this reason, urinary hydroxyproline has been used extensively as an amino acid marker for collagen degradation; Singer, F. R. et al., Metabolic Bone Disease, Vol. II (eds. Avioli, L. V., and Kane, S. M.), 489–575 (1978), Academic Press, New York.

U.S. Pat. No. 3,600,132 discloses a process for the determination of hydroxyproline in body fluids such as serum, urine, lumbar fluid and other intercellular fluids in order to monitor deviations in collagen metabolism. The patent states that hydroxyproline correlates with increased collagen anabolism or catabolism associated with pathological conditions such as Paget's disease, Marfan's syndrome, osteogenesis imperfecta, neoplastic growth in collagen tissues and in various forms of dwarfism.

Bone resorption associated with Paget's disease has also been monitored by measuring small peptides containing hydroxyproline, which are excreted in the urine following degradation of bone collagen; Russell et al., Metab. Bone Dis. and Rel. Res. 4 and 5, 2250262 (1981), and Singer, F. R., et al., supra.

In the case of Paget's disease, the increased urinary hydroxyproline probably comes largely from bone degradation; hydroxyproline, however, generally cannot be used as a specific index for bone degradation. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline.

Furthermore, about 80% of the free hydroxyproline derived from protein degradation is metabolised in the liver and never appears in the urine. Kiviriko, K. I., Int. Rev. Connect. Tissue Res. 5:93 (1970), and Weiss, P. H. and Klein, L., J. Clin. Invest. 48:1 (1969). Hydroxyproline is a good marker for osteoporosis as it is specific for collagen in bones even if it is not specific for bone resorption, but it is troublesome to handle.

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markers of bone resorption; Krane, S. M. and Simon, L. S., Develop. Biochem. 22:185 (1981).

Other researchers have measured the cross-linking compound 3-hydroxypyridinium in urine as an index of collagen degradation in joint diseases. See, for background and as examples, Wu and Eyre, Biochemistry, 23:1850 (1984): Black et al., Annals of the Rheumatic Diseases, 45:969–973 (1986); and Seibel et al., The Journal of Dermatology, 16:964 (1989). In contrast to the present invention, these prior researchers have hydrolysed peptides from body fluids and then looked for the presence of free 3-hydroxypyridinium residues.

Assays for determination of the degradation of type I, II, and III collagen are disclosed in EP-0394296 and U.S. Pat. No. 4,973,666 and U.S. Pat. No. 5,140,103. However, these patents are restricted to collagen fragments containing the cross-linker 3-hydroxypyridinium. Furthermore, the above mentioned assays require tedious and complicated purifications from urine of collagen fragments containing 3-hydroxypyridinium to be used for the production of antibodies and for antigens in the assays.

At present very few clinical data using the approach described in U.S. Pat. No. 4,973,666 and U.S. Pat. No. 5,140,103 are available. Particularly, no data concerning the correlation between the urinary concentration (as determined by methods described in the above mentioned patents) of 3-hydroxypyridinium containing telopeptides of type I collagen and the actual bone loss (as determined by repeated measurements by bone densiometry) have been published. The presence of 3-hydroxypyridinium containing telopeptides in urine requires the proper formation in bone tissue of this specific cross-linking structure at various times before the bone resorbing process. Very little information on these processes is available and it would be desirable to avoid this dependence of the correct formation of the cross-linking structure.

GB Patent Application No. 2205643 reports that the degradation of type III collagen in the body can be quantitatively determined by measuring the concentration of an N-terminal telopeptide from type III collagen in a body fluid. This method uses antibodies generated to N-terminal telopeptides released by bacterial collagenase degradation of type III collagen, said telopeptides being labelled and used in the assay.

Schröter-Kermani et al., Immunol. Invest. 19:475–491 (1990) describe immunological measurement systems based on CNBr fragments of collagen type I and II. Use is made of pepsin-solubilised collagen, leaving the telopeptides in the tissue (cf. the above mentioned GB Patent Application No. 2205643). There is therefore no conformity between the fragments and the antibodies raised therefrom. Further, the reference only describes measurements on extracted tissue samples.

The development of a monoclonal antibody raised against pepsin-solubilised type I collagen is described in Werkmeister et al., Eur. J. Biochem. 1987:439–443 (1990). The antibody is used for immunohistochemical staining of tissue segments and for measuring the collagen content in cell cultures. The measurements are not carried out on body fluids.

EP Patent Application No. 0505210 describes the development of antibody reagents by immunisation with purified cross-linked C-terminal telopeptides from type I collagen. The immunogen is prepared by solubilising human bone collagen with bacterial collagenase. The antibodies thus prepared are able to react with both cross-linked and non-cross-linked telopeptides, and cross-linkers other than pyridinoline.

International Patent Application No. WO 91/09114 discloses certain synthetic peptides which are used to promote cellular adhesion to a solid substrate. The use of the synthetic peptides as immunological reagents is not mentioned.

There are a number of reports indicating that collagen degradation can be measured by quantitating certain procollagen peptides. Propeptides are distinguished from telopeptides and alpha-helical region of the collagen core by their location in the procollagen molecule and the timing of their cleavage in vivo; see U.S. Pat. No. 4,504,587; U.S. Pat. No. 4,312,853; Pierard et al., Analytical Biochemistry 141:127–136 (1984); Niemela, Clin. Chem. 31/8:1301–1304 (1985); and Rohde et al., European Journal of Clinical Investigation, 9:451–459 (1979).

EP Patent Application No. 0298210 and No. 0339443 both describe immunological determination of procollagen peptide type III and fragments thereof. Further, a method based on the measurement of procollagen is disclosed in EP Patent Application No. 0465104.

The use of synthetic peptides with sequences derived from type IX collagen for the development of immunological reagents is disclosed in PCT Patent Application No. WO90/08195. Likewise the application describes the use of the antibodies thus produced for the determination of type IX collagen fragments in body fluids.

U.S. Pat. No. 4,778,768 relates to a method of determining changes occurring in articular cartilage involving quantifying proteoglycan monomers or antigenic fragments thereof in a synovial fluid sample.

Dodge, J. Clin Invest 83:647–661 (1981) discloses methods for analysing type II collagen degradation utilising a polyclonal antiserum that specifically reacts with unwound alpha-chains and cyanogen bromide-derived peptides of human and bovine type II collagens. The degradation products of collagen were not detected in a body fluid, but histochemically by staining of cell cultures, i.e. by "in situ" detection.

WO94/03813 describes a competitive immunoassay for detecting collagen or collagen fragments in a sample wherein a binding partner containing a synthetic linear peptide corresponding to the non-helical C-terminal or N-terminal domain of collagen is incubated with an antibody to the linear synthetic peptide and the sample, and wherein the binding of the antibody to the binding partner is determined.

WO95/08115 relates to assay methods in which collagen fragments in a body fluid are determined by reaction with an antibody which is reactive with a synthetic peptide. The assay may be a competition assay in which the sample and such a peptide compete for an antibody, possibly a polyclonal antibody raised against fragments of collagen obtained by collagenase degradation of collagen. Alternatively, it may be an assay in which an antibody, possibly a monoclonal antibody, is used which has been raised against such a synthetic peptide.

SUMMARY OF THE INVENTION

One particular peptide fragment which we have found in body fluid, particularly urine, is of the formula:

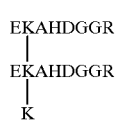

Formula 1

In the above formula, K—K—K represents cross-link which may for instance be a hydroxypyridinium cross-link but may be any naturally occurring cross-link and specifically any of those discussed in the above referenced paper of Last et al.

A larger peptide fragment including the above smaller fragment is reported in EP 0394296 and the above fragment is reported in WO 91/08478.

As shown in WO96/12133 we have also discovered that a proportion of the "peptide" fragments in body fluid are related to peptides of equivalent amino acid sequence, e.g. peptides of formula 1, by the isomerization of the linkage of aspartic acid in the formula to isoaspartic acid. We put "peptides" in quotes here as of course the isomerization means that these species are not longer properly regarded as being peptides.

The isomerization of proteins containing aspartic acid has been reported previously to be a spontaneous reaction occurring under physiological conditions.

See for instance Brennan et al Protein Science 1993, 2, 331–338, Galletti et al, Biochem, J. 1995, 306, 313–325, Lowenson et al, Blood Cells 1988, 14, 103–117 and Oliya et al, Pharmaceutical Research, Vol. 11, No. 5, 1994, p. 751.

The isomerization has the effect of transferring that part of the peptide chain which runs downstream of the aspartic acid residue in the carboxy terminus direction from the alpha carboxylic acid of the aspartic acid to which it is bonded via a peptide bond in the normal protein to the side chain carboxylic acid in a non-peptide amide bond, as shown below:

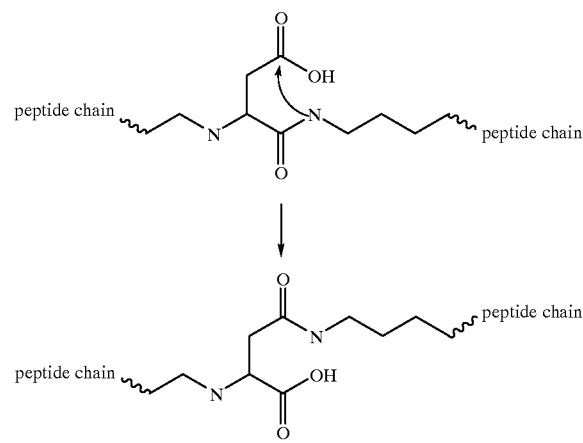

The non-peptide bonded aspartic acid residue is termed "isoaspartic acid".

Similar isomerization can occur in proteins containing asparagine residues (i.e. with —NH$_2$ instead of —OH in the starting protein in the above reaction scheme) and in glutamic acid and glutamine.

The above discovery indicates that this isomerization also occurs in bone tissue and the extent of isomerization is expected therefore to be marker for the age of the bone tissue concerned.

Furthermore, the presence amongst such bone peptide fragments of the isomerized peptides provides confirmation that the fragments indeed derive from bone degradation and not some other source such as the degradation of newly formed collagen never incorporated into bone.

It is believed that as disclosed by Geiger & Clarke in J. Biol. Chem (1987) 262(2):785–794, the isomerisation proceeds via a succinimidyl intermediate and that from this intermediate D-optically active forms of both the normal and isomerised forms of aspartic acid may also be produced. Of course, the amino acids normally present in proteins, including aspartic acid, are present in their L-optically active form.

We have now discovered that it is possible to develop immunoassays specific for proteins or their breakdown products in which D-amino acids, especially D-aspartic acid, are present in place of the normal L-form. In the context of collagen degradation this is believed to provide a further marker for the age of the collagen involved.

Accordingly, the present invention now provides in a first aspect a method of measurement of the rate of degradation of a body protein such as collagen, e.g. from bone, comprising determining the amount of one or more D-amino acid containing species in a body fluid by the reaction of said species with an immunological binding partner capable of distinguishing said D-amino acid containing species from the corresponding L-amino acid containing species.

The D-amino acid containing species (peptide analogues) in question may be characteristic of type I, type II or type III collagen, but preferably are characteristic of type I collagen.

The D-amino acid contained in said species may preferably be D-aspartic acid, D-asparagine, D-glutamic acid or D-glutamine and may be bonded via a normal peptide bond or in its iso-form.

More preferably, such a method determines the amount of one or more specific D-aspartic acid or D-isoaspartic acid containing peptide analogues present in said body fluid.

Preferably, the method determines the amount of a peptide analogue of formula 2 (below) present in said body fluid:

Formula 2 wherein one or both of D* is D-aspartic acid or D-isoaspartic acid, or of one or more peptide analogues incorporating an epitope present in a peptide analogue of formula 2 which contains D-aspartic acid or D-isoaspartic acid. EKAH GGR is SEQ.ID.No.1 in the attached sequence listing.

In the above formula, K—K—K is a cross-link such as a hydroxypyridinium cross-link which may be pyridinoline (which may be glycosylated or non-glycosylated) or deoxypyridinoline, or any other collagen cross link.

Preferably, said determination is carried out using an immunological binding partner specific for a D-isoaspartic acid containing species present in the sample during the procedure, preferably said isomerized peptide analogue of formula 2 or a isomerized peptide incorporating an epitope present in the isomerized peptide analogue of formula 2 which contains D-isoaspartic acid.

The immunological binding partner may be a monoclonal or polyclonal antibody. By the requirement that the immunological binding partner be specific for the D-optically active amino acid containing species is meant that the immunological binding partner distinguishes between said species and the analogous L-amino acid or L-isoamino acid containing species to an extent useful in the assay.

Suitable immunological binding partners also include fragments of antibodies capable of binding the same antigenic determinant including Fab, Fab' and F(ab')$_2$, fragments.

Preferably, the immunological binding partner is an antibody raised against a linear D-peptide analogue or isomerized peptide analogue, preferably a synthetic D-peptide analogue or isomerized peptide analogue, corresponding to a sequence within collagen with a D-amino acid, e.g. D-aspartic acid or D-isoaspartic acid substituting in said amino acid sequence for the corresponding L-amino acid, e.g. aspartic acid, in said collagen protein sequence.

The assay may take many forms including but not limited to heterogeneous assays e.g. ELISA and, RIA and homogeneous assays, e.g. turbidimetric assays, procedures for which are too well known to warrant description here.

In a second aspect, the invention includes the use in an assay for collagen derived peptides or isomerized peptides of a synthetic peptide analogue or isomerized peptide analogue having an amino acid sequence corresponding to a sequence within collagen with a D-amino acid, e.g. D-aspartic acid or D-isoaspartic acid, substituting in said amino acid sequence for the corresponding L-amino acid, e.g. L-aspartic acid, in said collagen protein sequence. In a competition assay, the said synthetic peptide analogue or isomerized peptide analogue may be used to compete for an immunological binding partner with one or more D-form peptide analogue or isomerised peptide analogues in the sample.

In an ELISA of this type, the D-form synthetic peptide analogue or peptide isomer analogue may be immobilised on a solid support. A sample may be incubated with a polyclonal antibody reactive with the synthetic peptide analogue or peptide isomer analogue in contact with the solid support and after washing, a peroxidase-conjugated (revealing) antibody may be added. After further incubation, a peroxidase substrate solution is added. By competition, D-form peptide analogue or peptide isomer analogue in the sample reactive with the antibody inhibits the peroxidase reaction.

Alternatively, the D-form synthetic peptide analogue or peptide isomer analogue may be used to raise a monoclonal immunological binding partner. The synthetic peptide analogue or isomerized peptide analogue need not then be a competing agent in the assay. For instance, collagenase treated collagen may be purified and immobilised onto the solid support and an ELISA may be carried out using a monoclonal antibody.

Accordingly, in a third aspect, the invention includes an antibody, preferably a monoclonal antibody, specific for an amino acid sequence corresponding to a sequence within a protein, e.g. collagen, with a D-amino acid, e.g. D-aspartic acid or isoaspartic acid, substituting in said amino acid sequence for the corresponding L-amino acid, e.g. aspartic acid, in said protein, e.g. collagen, sequence.

In a preferred embodiment of this aspect of the invention, the antibody is specific for a peptide analogue sequence or an isomerized peptide analogue sequence including the sequence EKAHD*GGR or EKAHiD*GGR (SEQ.ID.No.1) an epitope included in either sequence and containing D*, wherein D* is D-aspartic acid or D-isoaspartic acid.

Accordingly, this aspect of the invention includes an antibody, preferably a monoclonal antibody, reactive with an epitope containing, contained in, or constituted by the peptide isomer sequence EKAHD*GGR or EKAHiD*GGR, (SEQ.ID.No.1), wherein iD* is D-isoaspartic acid and D* is D-aspartic acid.

The whole of the octapeptide sequence is not needed to define the relevant epitope and the heptapeptide KAHD*GGR (SEQ.ID.No.2) or the hexapeptide AHD*GGR (SEQ.ID.No.2) may be used, even though the latter does not include the crosslink site.

In a fourth aspect, the invention provides an antibody, preferably a monoclonal antibody, raised against a peptide analogue or peptide-isomer analogue having an amino acid sequence corresponding to a sequence within a protein, e.g. collagen, with a D-amino acid, e.g. D-aspartic acid or D-isoaspartic acid, substituting in said amino acid sequence for the corresponding L-amino acid, e.g. L-aspartic acid in said collagen protein sequence.

The invention includes cell lines producing monoclonal antibodies according to the third or fourth aspects of the invention.

The invention also includes antibodies according to the third or fourth aspects of the invention coupled to a detectable marker. Suitable detectable markers include, but are not limited to, enzymes, chromophores, fluorophores, coenzymes, enzyme inhibitors, chemiluminescent materials, paramagnetic materials, spin labels, radio-isotopes, nucleic acid or nucleic acid analogue sequences.

In a fifth aspect, the invention includes the use in an assay for collagen or other protein derived peptides of an antibody specific for an amino acid sequence corresponding to a sequence within the protein, (e.g. collagen) with a D-amino acid, e.g. D-aspartic acid or D-isoaspartic acid, substituting in said amino acid sequence for the corresponding L-amino acid, e.g. aspartic acid, in said protein (e.g. collagen) sequence to obtain information regarding the amount of D-aspartic acid or D-isoaspartic acid containing peptide analogue or peptide isomer analogue in said body fluid.

In a sixth aspect, the invention includes a synthetic peptide isomer having an amino acid sequence corresponding to a sequence within collagen with a D-amino acid, e.g. D-aspartic acid or D-isoaspartic acid, substituting in said amino acid sequence for the corresponding L-amino acid, e.g. L-aspartic acid, in said collagen protein sequence, preferably in at least the substantial absence of the corresponding all L-peptide.

Preferably there is a glycine residue adjacent the D-amino acid residue site in the native peptide form of the amino acid sequence, as an adjacent glycine facilitates the racemisation of aspartic acid and other relevant amino acids.

Antibodies may be prepared which are respectively selective for one or more L-aspartic acid containing peptides and for their D-aspartic acid or D-isoaspartic acid containing analogues. It is then possible to carry out an assay for both D and L variants of the peptide or peptides. The relative amount of D-amino acid will provide an indication of the age of the protein which is being broken down and of the bone if the assay is for a type I collagen fragment. Accordingly, in a seventh aspect the invention provides a method of obtaining information regarding collagen resorption in a patient, comprising measuring in a body fluid the relative amounts of at least one L-amino acid, e.g. L-aspartic acid, containing peptide derived from collagen and a corresponding D-amino acid, e.g. D-aspartic acid or D-isoaspartic acid containing peptide analogue. This will include assays for the turnover of cortical bone and of trabecular bone separately based upon their different D-form content and the use of the resulting information in assessing the effect of therapies.

The invention also includes test kits useful in the methods described above. Such kits may comprise an antibody according to the third or fourth aspect of the invention, or similarly specific antibody fragment, preferably in combination with any one or more of:

- a synthetic peptide analogue containing a D-amino acid such as D-aspartic acid or D-isoaspartic acid reactive with the antibody,
- an antibody-enzyme conjugate and/or a substrate therefor,
- an enzyme conjugate-substrate reaction stopping composition, or
- a wash solution.

The invention may be applied both to humans and to animals.

Suitable body fluids include, human or animal urine, blood, serum, plasma and synovial fluid. It is contemplated that the method may also be used e.g. on saliva and sweat. The body fluid may be used as it is, or it may be purified prior to the contacting step. This purification step may be accomplished using a number of standard procedures, including, but not limited to, cartridge adsorption and elution, molecular sieve chromatography, dialysis, ion exchange, alumina chromatography, hydroxyapatite chromatography, and combinations thereof.

We shall refer to the normally peptide bonded L-aspartate containing form of a protein or peptide as $\alpha_L$ and to the isomerised form as $\beta_L$. We shall refer to peptides or proteins containing D-aspartate bonded in the normal manner as $\alpha_D$ and to the isomerised form as $\beta_D$.

It is believed that isomerisation occurs via a succinimide intermediate and that the rate of spontaneous racemisation of the succinimide intermediate is much greater than that of either $\alpha_L$ or $\beta_L$. Thus, not only should the amount of $\beta_L$ be a marker for the age of protein derived species but so should the amount of $\beta_D$ and that of $\alpha_D$, since all these forms are provided via the same succinimide intermediate.

We show below that there is a clear, correlation in urine in the amounts of $\alpha_L$, $\beta_L$, and $\beta_D$ forms of a selected peptide in samples taken from postmenopausal women. A similar correlation with $\alpha_D$ is also to be expected. Also, we show below that urine values of $\alpha_L$, $\beta_L$ and $\beta_D$ forms of the peptide fall to essentially the same extent in response to bisphosphonate therapy which reduces bone resorption. Measurements of $\alpha_D$ peptide would behave similarly. If such measurements are conducted in serum however, only the $\alpha_D$, $\beta_L$ and $\beta_D$ forms would be expected to reflect the bisphosphonate treatment since a shown in PCT/EP96/01228, measurements of the $\alpha_L$ form in serum do not. This is probably because there is a high background of the $\alpha_L$ form of the peptide derived from sources other than the breakdown of collagen incorporated in bone.

The peptide used in the Examples below is (in its $\alpha_L$ form), EKAHDGGR (SEQ.ID.No.1) (Glu.Lys.Ala.His.Asp.Gly.Gly.Arg) and in body fluids such as urine may be present as part of a variety of larger peptides which may include cross-links of the various types formed in collagen. It derives from the non-helical C-terminal part of type I collagen.

BRIEF DESCRIPTION OF THE DRAWINGS

The invention is illustrated with reference to specific Examples below. Reference is made to the appended drawings, in which.

DETAILED DESCRIPTION OF THE INVENTION

Figure 1:
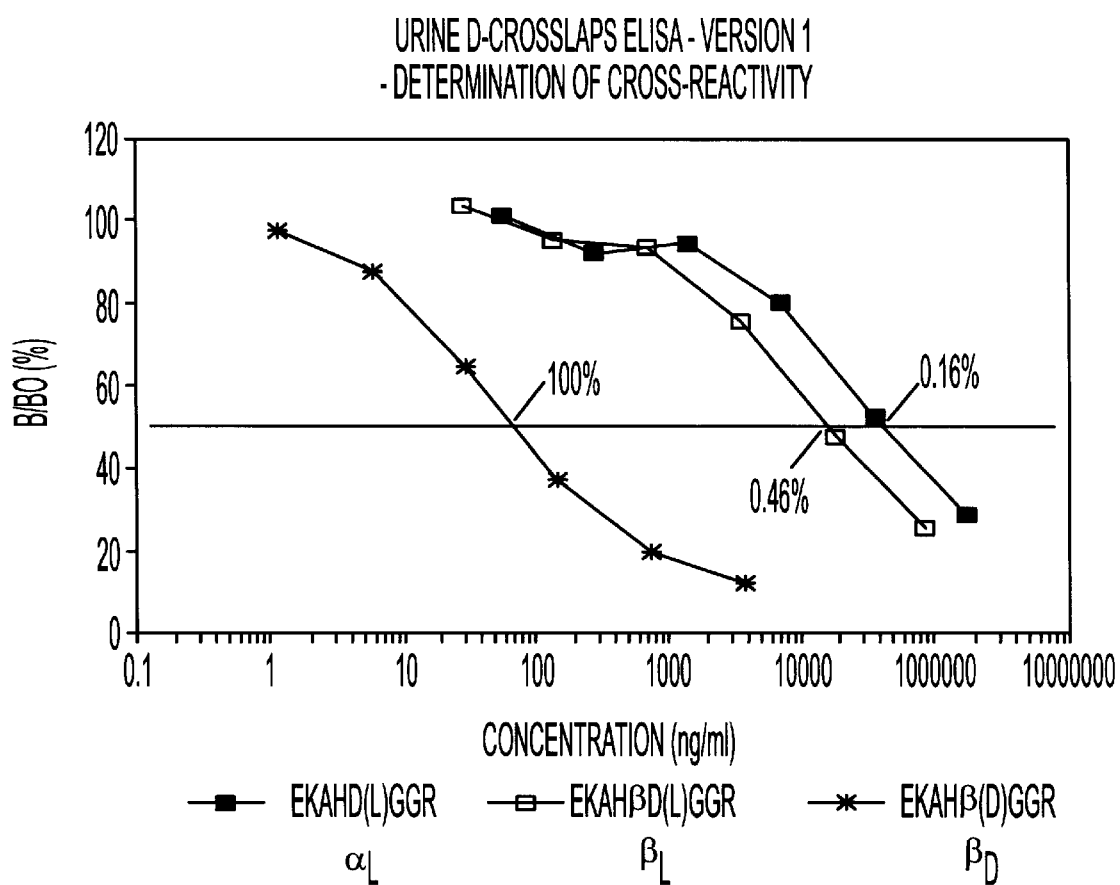
FIG. 1 shows the results obtained in Example 1 depicted graphically.

In a preferred embodiment of the method according to the invention, the assaying of type I, II or III collagen fragments in urine or other body fluid is performed by an inhibition ELISA (enzyme linked immunosorbent assay) by metering off a sample of urine or other body fluid, contacting the sample with a synthetic peptide D-analogue having a sequence derived from collagen and with an antibody, which is immunoreactive with the synthetic peptide D-analogue. The synthetic peptide D-analogue is immobilised on a solid support. The antibody may be raised against the synthetic peptide D-analogue or may be raised against collagen degradation products.

Preparation of Synthetic Peptide D-analogues

The preparation of synthetic peptides and peptide D-analogues may be performed according to procedures well known in the art, e.g. by solid-phase peptide synthesis techniques commonly described as "Merrifield synthesis". Also classical solution phase techniques may be used. Sequences of interest include potential sites for collagen cross-linking (see for example Kühn, K., in Immunochemistry of the extracellular matrix, 1:1–29(1982), Eyre, D. R., Ann. Rev. Biochem. 53:717–48 (1984), or U.S. Pat. No. 5,140,103). Examples of such peptides sequences are given in Table 1 below. The conventional peptide synthesis method applied to aspartic acid containing peptides, but using D-aspartic acid, may produce a mixture of peptide (with normal peptide bonded aspartic acid $\alpha_D$) and peptide analogue with isomerization of the bonding to the aspartic acid ($\beta_D$). Generally such a mixture will be satisfactory as one of the $\alpha_D$ and $\beta_D$ forms will be inert in the assay depending on the specificity of the antibody used. However, heating such a mixture will normally produce isomerization of the peptide content to the iso-form.

Regarding the synthetic peptide analogues, it is possible to omit (or add) one or more amino acid residues from (or to) the crosslinkable site sequences without substantial loss of the ability to (a) raise antibodies recognising the $\alpha_D$ or $\beta_D$ analogue of the corresponding native collagen fragment or (b) inhibit the binding of such antibodies to the said analogue of the native fragment. It is possible to use longer collagen fragments and/or chimeric peptide analogues to raise the antibodies and, in principle, it is not necessary to use the same peptide analogue as the immunogen and the competitor in a competition assay.

TABLE 1

Examples of Amino Acid Sequences with Potential Sites for Cross-linking in Various Types of Collagen to be Used as a Basis for $\alpha_D$ or $\alpha_D$ synthetic peptide analogues according to the present invention Collagen Type I Potential sites
in telopeptide analogues: N                                    C
α1 (I)    N-term.Asp-Glu-Lys-Ser-Thr-Gly-Gly
          (α1(I)N1) SEQ.ID.No.4
α1 (I)    C=term.Glu-Lys-Ala-His-Asp-Gly-Gly-Arg
          (α1(I)C1) SEQ.ID.No.1
α2 (I)    N-term.Gln-Tyr-Asp-Gly-Lys-Gly-Val-Gly
          (α2(I)N1) SEQ.ID.No.5

Collagen Type II

Potential sites
in telopeptide analogues: N                                    C
α1 (II)   N-term. Gly-Asp-Ile-Lys-Asp-Ile-Val
          SEQ.ID.No.6
α1 (II)   C-term. Glu-Lys-Gly-Pro-Asp
          SEQ.ID.No.7

Collagen Type III

Potential sites
in telopeptide analogues: N                                    C
α1 (III)  N-term. Asp-Val-Lys-Ser-Gly-Val
          SEQ.ID.No.8

Preparation of Antibodies

The methods for preparation of both monoclonal and polyclonal antibodies are well known in the art. For example, see Campbell, A. M., Laboratory Techniques in Biochemistry and Molecular Biology, Vol. 12 (1986). It is possible to produce antibodies to synthetic $\alpha_D$ or $\beta_D$ peptide analogues by immunisation. However, because of the relatively small molecular weight of these compounds it is preferred that the hapten be conjugated to a carrier molecule. Suitable carrier molecules include, but are not limited to, bovine serum albumin, thyroglobulin, ovalbumin, tetanus toxoid, and keyhole limpet hemocyanin. The preferred carrier is bovine serum albumin. To present the hapten in its most immunogenic form to the antibody producing cells of the immunised animal a number of alternative coupling protocols can be used. Suitable procedures include, but are not limited to, glutaraldehyde, carbodiimide, and periodate. Preferred binding agents are glutaraldehyde and carbodiimide.

The preparation of antibodies may be carried out by conventional techniques including immunisation with collagen fragments containing natural racemisation and optionally isomerization or synthetic D-form peptide analogues conjugated to a carrier. To improve the immunogenicity it is preferred that the immunogen be mixed with an adjuvant before injection. Examples of adjuvants include, but are not limited to, aluminium hydroxide, Freund's adjuvant, and immune-stimulating complexes (ISCOMs). ISCOMs can be made according to the method described by Morein, B. et al., Nature 308:457–460 (1984).

Either monoclonal or polyclonal antibodies to the hapten-carrier molecule can be produced. For the production of monoclonal antibodies it is preferred that mice are immunised. Spleen cells from the immunised mouse are harvested, homogenised, and thereafter fused with cancer cells in the presence of polyethylene glycol to produce a cell hybrid which produces monoclonal antibodies specific for isomerized peptide fragments derived from collagen. Suitable cancer cells include, but are not limited to, myeloma, hepatoma, carcinoma, and sarcoma cells. Detailed descriptions of the production of monoclonal antibodies are provided in Goding, J. W., in Monoclonal Antibodies: Principles and Practice, (1986). A preferred preliminary screening protocol comprises the use of synthetic D-peptide analogue conjugated to a carrier and coated on to the solid surface of a microtiter plate.

For the preparation of polyclonal antibodies which are reactive with D-peptide analogue fragments derived from collagen, different animal species can be immunised. Suitable species include, but are not limited to, chicken, rabbit and goat. Chicken and rabbit are preferred.

Antibodies so produced may be screened for suitability for use according to the invention by testing for reactivity with a D-amino acid containing synthetic peptide analogue of appropriate sequence.

Antibody fragments are prepared by methods known in the art (see E. Ishikawa, Journal of Immunoassay 3:209–327 (1983)).

Conduct of Immunoassays

Accordingly, by utilisation of an immunoassay with the antibodies prepared as above it is possible to assay a biological fluid sample without prior fractionation or hydrolysis. The specificity for the desired collagen fragments in the biological fluid may be supplied by the antibody in combination with the use of a synthetic D-peptide analogue (against which the antibody was raised or in any event with which the antibody is immunochemically reactive) in the assay construction.

As an alternative the immunoassay may be performed using a monoclonal antibody. The basic idea of this assay design is to shift the specificity of the assay from the antigen (synthetic peptide analogue of collagen) to the antibody (from rabbit antiserum to monoclonal antibody). Using this construction the assay does not need to make further use of a synthetic peptide analogue. This version of the immunoassay is suitably performed by incubating the patient sample of a standard solution with a peroxidase-conjugated antibody solution in a microtiter plate precoated with purified collagenase-treated collagen. After washing, the wells of the plate are incubated in the dark with a substrate solution. The colour reaction is stopped by the addition of a stopping solution, and finally the absorbance is measured.

The immunoassays themselves may be conducted using any procedure selected from the variety of standard assay protocols generally known in the art. As it is generally understood, the assay is constructed so as to rely on the interaction between the specific immunological binding partner and the desired analyte for specificity and to utilise some means to detect the complex formed by the analyte and the immunological binding partner. The immunological binding partner may be complexed to a solid support and used as a capture immunological binding partner for the analyte. This protocol may be run in a direct form, wherein the formation of analyte-immunological binding partner complex is detected, e.g. by a fluorescent, radioactive or enzymatic label, or it may be run in a competitive format wherein a labelled standard competes with the analyte for the immunological binding partner. The format may also be constructed as an agglutination assay or the complex may be precipitated by addition of a suitable precipitant to the reaction mixture. The specific deign of the immunoassay protocol is open to a wide variety of choice, and the number of clinical assay devices and protocols avail-able in the art is multitudinous. For a variety of such protocols, see U.S. Pat. No. 5,001,225.

A homogeneous assay format may be used in which for instance latex particles are conjugated to the peptide or isomerised peptide and the sample and the particles compete to bind the antibody. Specific agglutination of the particles by antibody produces a change which is optically detectable as a change in scattering or absorbance and which is inhibited by crosslinks in the sample.

The antibodies and revealing reagents for the conduct of an immunoassay using standard detection protocols, for example radioisotope labelling, fluorescent labelling or ELISA, either in a direct or competitive format, may conveniently be supplied as kits which include the necessary components and instructions for the assay. In one embodiment of the invention such a kit includes a microtiter plate coated with a relevant synthetic peptide D-analogue, standard solutions for preparation of standard curve, a body fluid (e.g. urine) control for quality testing of the analytical run, rabbit antibodies reactive with the above mentioned synthetic peptide D-analogue, anti-rabbit immunoglobulins conjugated to peroxidase, a substrate solution, a stopping solution, a washing buffer and an instruction manual.

Since immunoassays can be constructed using antibodies and specific synthetic peptide D-analogues, the ratios of the corresponding collagen fragment sequences in an appropriate biological fluid can be determined as well as their individual levels and their total. Thus, the assay can be designed to include antibodies which will result in determination of several peptide D-analogues and optionally the native peptide sequences or determination of a single D-amino acid containing peptide analogue sequence, or any desired combination thereof.

In addition to the use of the herein specified peptide D-analogues as indicators of bone resorption, bone metabolic balance is advantageously determined by the substantially simultaneous determination of a marker of the formation of bone in the same or other appropriate biological fluid from the same individual. "Substantially simultaneous" means the same day, preferably within 4 hours. For example such markers include osteocalcin (also known as bone GLA protein of BGP), propeptides of procollagen type I, bone alkaline phosphatase and total alkaline phosphatase. Suitable methods for the determination of these markers can be found, for example, in Delmas, P. D., et al., J. Bone Min. Res. (1986) 1:333–337.

The assay of the present invention which provides an index to determination of the metabolic status of tissues, which generate collagen-derived peptides and peptide analogues when degradation occurs, is useful in a variety of contexts. First, when considering the degradation of type I collagen, the assays are methods to assess an abnormal condition of a subject by indicting, for example, excessive bone resorption. This may show the presence of an osteoporotic condition or the metastatic progress of a malignancy. Other conditions characterised by excessive bone resorption include Paget's disease and hyperparathyroidism. Likewise, a number of other disease states involving connective tissue may be monitored by determination of the degradation of collagen. Examples are collagen type II degradation associated with rheumatoid arthritis and osteoarthritis and collagen type III degradation in vasculitis syndrome. Since the condition of the subject can be monitored continuously, application of these assays can also be used to monitor the progress of therapy administered to treat these or other conditions. Further, the assays can be used as a measure of toxicity, since the administration of toxic substances often results in tissue degradation.

Thus the assays may be applied in any situation wherein the metabolic condition of collagen tissues can be used as an index of the condition, treatment, or effect of substances directly administered to the subject or to which the subject is exposed in the environment.

EXAMPLES

The following examples are intended to illustrate, but not to limit the invention.

In these Examples the following antibodies and assay protocols are used:

(a) $\alpha_L$ CROSSLAPS RIA: This assay employs in RIA format a monoclonal antibody raised against the peptide EKAHDGGER [SEQ.ID.NO.1] (all L- and normally peptide bonded).

(b) $\beta_L$ CROSSLAPS ELISA: This assay in ELISA format utilises a rabbit antiserum produced by immunisation with bacterial collagenase treated bone collagen (CTC) and spontaneously having essentially no reactivity to the peptide EKAHDGGR in its normal $\alpha_L$ form and essentially no reactivity to the $\beta_D$ analogue of said peptide.

(c) $\beta_D$ CROSSLAPS ELISA: This assay in ELISA format again utilises a rabbit antiserum to CTC but one selected for an unusual spontaneous pattern of specificity. Forty three rabbits were immunised and antisera were obtained. These were screened for specificity to the $\beta_D$ analogue of the peptide EKAHDGGR (SEQ.ID.No.1) (i.e. EKAH$\beta_D$DGGR). One antiserum was selected that had the greatest specificity for this peptide analogue.

The ELISA format used was as follows:

The polyclonal ELISA is based on an immobilised synthetic peptide analogue with an amino acid sequence of eight amino acids (8AA) characteristic of an isomerised part of the C-telopeptide of the α1-chain of type I collagen (Glu-Lys-Ala-His-Asp-Gly-Gly-Arg-) (SEQ.ID.No.1) in L or D form. During incubation with an antibody reactive with this sequence, a competition takes place between the immobilised peptide $\beta_D$ or $\beta_L$ analogue and the breakdown products of the α1-chain of type I collagen in the sample.

Briefly, a 25 μl sample or standard is added to each well of a formula 1 antigen-coated microplate, followed by 100 μl of antiserum raised against collagenase treated type 1 collagen. The plates are incubated for 1 hour at room temperature under agitation and washed five times with a washing buffer. A goat anti-rabbit immunoglobulin G horseradish peroxidase conjugate (100 μl) is added to each well. After incubation for 1 hour at room temperature, plates are washed five times as before. The enzyme substrate (100

μl/well) is added, and after 30 minutes of incubation in the dark, the reaction is stopped by adding 100 μl 0.18M $H_2SO_4$. The optical density of 450 nm is measured with a microplate reader. Duplicate measurements are performed for each sample, and the data are expressed as nanograms per mol creatinine (Cr), measured by a standard colorimetric technique.

Example 1

Specificity of $\beta_D$ CROSSLAPS ELISA: Cross-reactivity to $\alpha_L$ and $\beta_D$ Forms of the Peptide EKAHDGGR and a Rabbit CTC Anti-serum Varying concentrations of the peptide EKAHDGGR (SEQ.ID.No.1) and its analogues EKAH$\beta_L$DGGR and EKAH$\beta_D$DGGR were formulated as samples and run in $\beta_D$ CROSSLAPS ELISA as described above. The results are shown in FIG. 1. Cross reactivity is calculated based on the concentration of sample needed to inhibit 50% of the signal generating binding to the plate in the assay. Compared to $\beta_D$, the cross-reactivity to both $\alpha_L$ and $\beta_L$ is below 0.5%, showing that the assay is highly specific for the $\beta_D$ form of the isomerised sequence which compared to the natural sequence has undergone both isomerisation and racemisation.

Example 2

Figure 2:
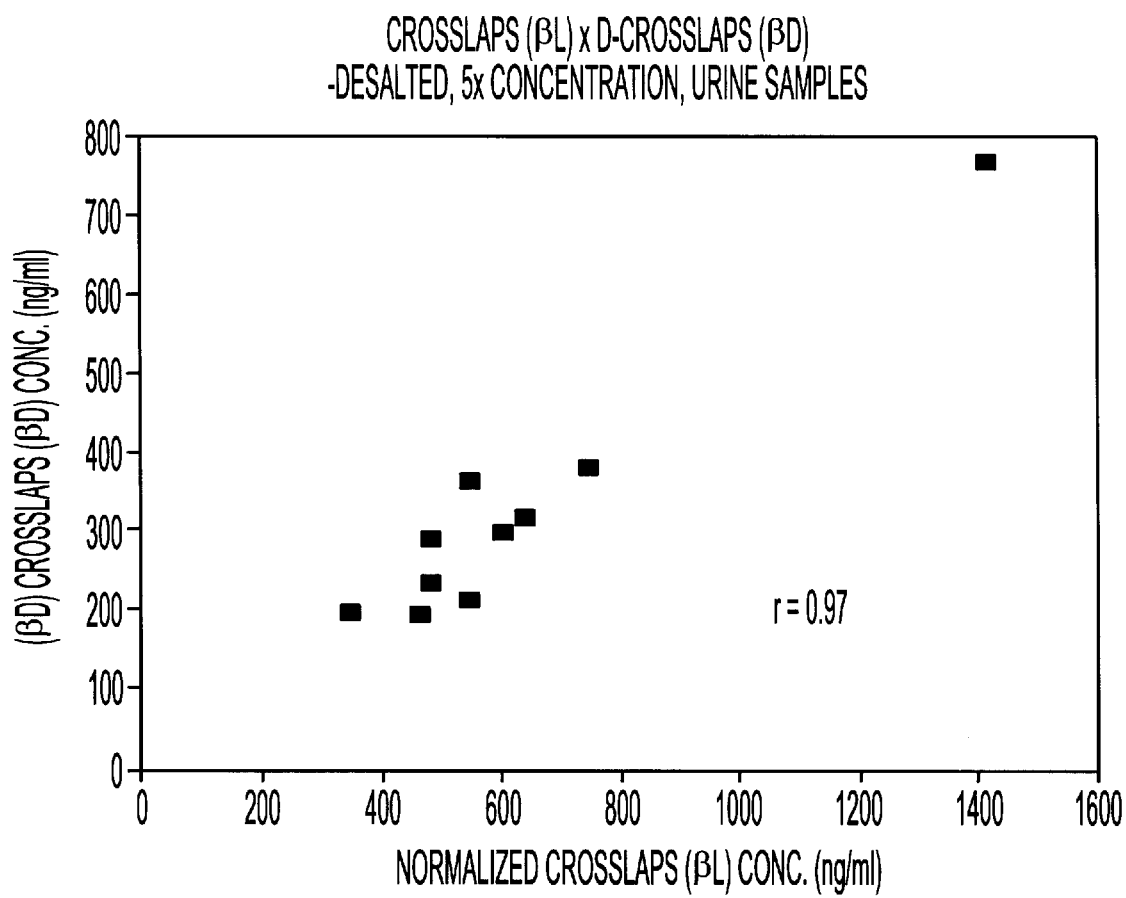
FIG. 2 shows the correlation between measurements of $\beta_L$ and $\beta_D$ forms of the peptide in urine samples.

Correlation Between Urine Measurements of by $\alpha_L$ CROSSLAPS RIA, $\beta_L$ CROSSLAPS ELISA and $\beta_D$ CROSSLAPS ELISA Urine samples from postmenopausal women were concentrated ×5 and desalted and subjected to the three assays described above. Results were as shown in Table 2 below and in FIG. 2. It can be seen that the results of the $\beta_L$ and $\beta_D$ assays show a correlation co-efficient of r=0.95 and that the $\beta_D$ concentration is approximately half that of $\beta_L$.

TABLE 2

| Sample No. | $\alpha_L$-CrossLaps RIA ng/ml | $\beta_L$ CrossLaps ELISA ng/ml | $\beta_D$-CrossLaps ELISA ng/ml |
| --- | --- | --- | --- |
| 1 | 6325 | 605 | 301 |
| 2 | 6720 | 548 | 216 |
| 3 | 5920 | 641 | 318 |
| 4 | 5300 | 485 | 291 |
| 5 | 4073 | 348 | 197 |
| 6 | 6845 | 486 | 236 |
| 7 | 8535 | 747 | 384 |
| 8 | 7985 | 549 | 366 |
| 9 | 16560 | 1414 | 774 |
| 10 | 5020 | 465 | 195 |

Example 3

Effect of 9 Months Bisphosphonate Therapy on Postmenopausal Women

The effect of bisphosphonate therapy (20 mg oral Alendronate, daily) was investigated on the urinary excretion of $\alpha_L$-, $\beta_L$-, and $\beta_D$ fragments using the $\alpha_L$-CrossLaps™ RIA, the $\beta_L$-CrossLaps™ ELISA, and the $\beta_D$-CrossLaps™ ELISA. Results are shown in Table 3. The last three columns show the percent decrease related to baseline values for all three fragments for each individual. As can be seen, the decreases are almost equal for the three different fragments but greatest for $\beta_D$. Consequently, these results strongly indicate that urinary $\beta_D$ fragments like the corresponding $\alpha_L$- and $\beta_L$ fragments are sensitive to bisphosphonate therapy and therefore may be used as a marker to estimate the rate of bone resorption.

TABLE 3

| | | Concentration corrected for creatinine | | | Effect of Bisphosphonate therapy | | |
| --- | --- | --- | --- | --- | --- | --- | --- |
| Patient | Months of treatment | $\alpha_L$ (ng/ml)/mM | $\beta_L$ (mg/ml)/mM | $\beta_D$ (ng/ml)/mM | $\alpha_L$ fall (%) | $\beta_L$ fall (%) | $\beta_D$ fall (%) |
| 1 | 0.5 | 317.74 | 262.98 | 8.345 | 91.93 | 90.25 | 96.93 |
| 1 | 9 | 25.64 | 25.64 | 0.256 | | | |
| 2 | 0.5 | 771.45 | 796.81 | 14.913 | 97.46 | 97.54 | 98.69 |
| 2 | 9 | 19.61 | 19.61 | 0.196 | | | |
| 3 | 0.5 | 594.05 | 402.33 | 28.791 | 84.83 | 91.39 | 97.52 |
| 3 | 9 | 90.12 | 34.64 | 0.714 | | | |
| 4 | 0.5 | 441.86 | 533.14 | 8.924 | 96.16 | 96.82 | 98.10 |
| 4 | 9 | 16.95 | 16.95 | 0.169 | | | |
| 5 | 0.5 | 888.87 | 742.74 | 19.653 | 79.57 | 80.84 | 76.37 |
| 5 | 9 | 181.56 | 142.33 | 4.644 | | | |
| 6 | 0.5 | 608.24 | 193.82 | 3.471 | 89.72 | 67.75 | 81.99 |
| 6 | 9 | 62.50 | 62.50 | 0.625 | | | |
| 7 | 0.5 | 803.30 | 789.90 | 12.625 | 86.63 | 89.14 | 95.83 |
| 7 | 9 | 107.37 | 85.79 | 0.526 | | | |
| 8 | 0.5 | 333.73 | 344.64 | 10.813 | 91.44 | 91.71 | 97.36 |
| 8 | 9 | 28.57 | 28.57 | 0.286 | | | |

What is claimed is:

1. A method of measuring the rate of degradation of a body protein, which comprises determining the amount of an analogue of a protein fragment in a body fluid by contacting the body fluid with an immunological binding partner, wherein the protein fragment contains an L-amino acid residue; the amino acid sequence of the analogue is the same as that of the protein fragment apart from a D-amino acid residue substituted in place of the L-amino acid residue; and the immunological binding partner is capable of distinguishing the protein fragment from the analogue.

2. The method of claim 1, wherein the D-amino acid residue is a residue of D-aspartic acid or D-isoaspartic acid.

3. The method of claim 2, wherein the protein fragment is a fragment of collagen.

4. The method of claim 3, wherein the analogue is of Formula 2 (below):

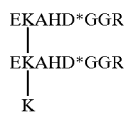

Formula 2 wherein K—K—K is any naturally occurring cross-link and D* is a residue of D-aspartic acid or D-isoaspartic acid, or wherein the analogue is an epitope present in Formula 2 that contains the residue of D-aspartic acid or D-isoaspartic acid.

5. The method of claim 1, wherein the immunological binding partner specifically binds to an analogue of a protein fragment in the body fluid, wherein said analogue contains a D-isoaspartic acid residue.

6. The method of claim 1, wherein the immunological binding partner is an antibody raised against a linear analogue of a collagen fragment containing an L-amino acid residue, wherein the linear analogue has an amino acid sequence that is the same as that of the collagen fragment apart from a D-amino acid residue substituted in place of the L-amino acid residue.

7. An antibody that specifically binds to an analogue of a protein fragment containing an L-amino acid residue, wherein the amino acid sequence of said analogue is the same as that of the protein fragment apart from a D-amino acid residue substituted in place of the L-amino acid residue.

8. The antibody of claim 7, wherein said analogue comprises the amino acid sequence AHD*GGR or AHiD*GGR or an epitope included in either sequence that contains D* or iD*, wherein D* is a residue of D-aspartic acid and iD* is a residue of D-isoaspartic acid.

9. An antibody raised against an analogue of a collagen fragment containing an L-amino acid residue, wherein the amino acid sequence of said analogue is the same as that of the collagen fragment apart from a D-amino acid residue substituted in place of the L-amino acid residue.

10. A cell line producing a monoclonal antibody that specifically binds to a peptide analogue sequence or peptide analogue isomer sequence comprising the amino acid sequence AHD*GGR or AhiD*GGR, or an epitope thereof containing D* or iD*, wherein D* is a residue of D-aspartic acid and iD* is a residue of D-isoaspartic acid.

11. The antibody of claim 7 coupled to a detectable marker.

12. A synthetic analogue of a collagen fragment containing an L-amino acid residue, wherein the amino acid sequence of said synthetic analogue is the same as that of the collagen fragment apart from a D-amino acid residue substituted in place of the L-amino acid residue.

13. The synthetic analogue of claim 12, wherein the L-amino acid residue is a residue of aspartic acid and is adjacent to a glycine residue.

14. A method of obtaining information regarding protein degradation in a patient, comprising measuring in a body fluid the relative amounts of at least one L-amino acid containing peptide derived from a protein and a corresponding D-amino acid containing peptide analogue.

15. A test kit for use in the method of claim 1, comprising an antibody or antibody fragment that specifically binds to an analogue of a protein fragment containing an L-amino acid residue, wherein the amino acid sequence of said analogue is the same as that of the protein fragment apart from a D-amino acid residue substituted in place of the L-amino acid residue, in combination with any one or more of:

a synthetic peptide analogue containing a D-aspartic acid residue or D-isoaspartic acid residue reactive with the antibody or antibody fragment;

an antibody-enzyme conjugate, a substrate therefor, or both;

an enzyme conjugate-substrate reaction stopping composition; or a wash solution.

16. A method of measuring the in vivo degradation of collagen, which comprises:

contacting a body fluid sample with an immunological binding partner, wherein the immunological binding partner specifically binds to an analogue of a collagen fragment, but does not specifically bind to the collagen fragment; and determining if anything within the body fluid sample specifically binds to the immunological binding partner;

wherein the collagen fragment contains an L-aspartic acid residue or an L-isoaspartic acid residue, and the analogue of the collagen fragment has the same amino acid sequence as the collagen fragment apart from a D-aspartic acid residue or D-isoaspartic acid residue substituted in place of the L-aspartic acid residue or L-isoaspartic acid residue.

17. The method of claim 16 wherein the collagen fragment is a fragment of collagen type I, II, or III.

18. The method of claim 17 wherein the analogue of the collagen fragment is of Formula 2:

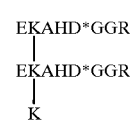

Formula 2 wherein K—K—K is any naturally occurring cross-link and D* is D-aspartic acid residue or D-isoaspartic acid residue, or wherein the analogue of the collagen fragment consists essentially of an epitope included in Formula 2 that contains a D-aspartic acid or D-isoaspartic acid residue.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
          (A) ORGANISM: homo sapiens (ix) FEATURE:
          (A) NAME/KEY: Modified-site
          (B) LOCATION:5
          (D) OTHER INFORMATION:/product= "Asp may be Asp, D-Asp, or
              iso-D-Asp"

(xi) SEQUENCE DESCRIPTION: SEQ ID NO: 1:

Glu Lys Ala His Asp Gly Gly Arg
1               5

(2) INFORMATION FOR SEQ ID NO: 2:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
          (A) ORGANISM: homo sapiens (ix) FEATURE:
          (A) NAME/KEY: Modified-site
          (B) LOCATION:4
          (D) OTHER INFORMATION:/product= "Asp may be D-Asp or
              iso-D-Asp"

(xi) SEQUENCE DESCRIPTION: SEQ ID NO: 2:

Lys Ala His Asp Gly Gly Arg
1               5

(2) INFORMATION FOR SEQ ID NO: 3:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: homo sapiens (ix) FEATURE:
             (A) NAME/KEY: Modified-site
             (B) LOCATION:3
             (D) OTHER INFORMATION:/product= "Asp may be D-Asp or
                 iso-D-Asp"

(xi) SEQUENCE DESCRIPTION: SEQ ID NO: 3:

Ala His Asp Gly Gly Arg
1               5

(2) INFORMATION FOR SEQ ID NO: 4:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: homo sapiens (xi) SEQUENCE DESCRIPTION: SEQ ID NO: 4:

Asp Glu Lys Ser Thr Gly Gly
1               5

(2) INFORMATION FOR SEQ ID NO: 5:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
         (A) ORGANISM: homo sapiens (xi) SEQUENCE DESCRIPTION: SEQ ID NO: 5:

Gln Tyr Asp Gly Lys Gly Val Gly
1               5

(2) INFORMATION FOR SEQ ID NO: 6:

(i) SEQUENCE CHARACTERISTICS:
         (A) LENGTH: 7 amino acids
         (B) TYPE: amino acid
         (C) STRANDEDNESS: single
         (D) TOPOLOGY: linear

```
        (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: homo sapiens (xi) SEQUENCE DESCRIPTION: SEQ ID NO: 6:

Gly Asp Ile Lys Asp Ile Val
1               5

(2) INFORMATION FOR SEQ ID NO: 7:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: homo sapiens (xi) SEQUENCE DESCRIPTION: SEQ ID NO: 7:

Glu Leu Gly Pro Asp
1               5

(2) INFORMATION FOR SEQ ID NO: 8:

(i) SEQUENCE CHARACTERISTICS:
             (A) LENGTH: 6 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
             (A) ORGANISM: homosapiens (xi) SEQUENCE DESCRIPTION: SEQ ID NO: 8:

Asp Val Lys Ser Gly Val
1               5
```